(12) United States Patent
Nakahata et al.

(10) Patent No.: US 8,395,017 B2
(45) Date of Patent: Mar. 12, 2013

(54) ABSORBENT ARTICLE HAVING EXTENSIBILITY AT WAIST PANEL

(75) Inventors: Hiroshi Nakahata, Kobe (JP); Hong Lu, Cincinnati, OH (US); Kouichi Miyamoto, Kobe Hyogo (JP); Takuya Shirakawa, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 1554 days.

(21) Appl. No.: 10/736,282

(22) Filed: Dec. 15, 2003

(65) Prior Publication Data

US 2004/0147890 A1    Jul. 29, 2004

Related U.S. Application Data

(63) Continuation of application No. PCT/US02/20427, filed on Jun. 28, 2002.

(60) Provisional application No. 60/302,431, filed on Jul. 2, 2001.

(30) Foreign Application Priority Data

Jun. 28, 2002    (WO) ............... PCT/US02/20427

(51) Int. Cl.
*A61F 13/15*    (2006.01)
*A61F 13/20*    (2006.01)

(52) U.S. Cl. ............... 604/382; 604/383; 604/385.3
(58) Field of Classification Search ............... 604/385.2, 604/382, 383, 385.3
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,662,875 A | 5/1987 | Hirotsu et al. | |
| 4,695,278 A | 9/1987 | Lawson | |
| 4,795,454 A | 1/1989 | Dragoo | |
| 4,808,178 A | 2/1989 | Aziz et al. | |
| 4,846,815 A | 7/1989 | Scripps | |
| 4,894,060 A | 1/1990 | Nestegard | |
| 4,909,803 A | 3/1990 | Aziz et al. | |
| 4,935,021 A | 6/1990 | Huffman et al. | |
| 4,946,527 A | 8/1990 | Battrell | |
| 4,963,140 A | 10/1990 | Robertson et al. | |
| 5,151,092 A | 9/1992 | Buell | |
| 5,221,274 A * | 6/1993 | Buell et al. | 604/385.3 |
| 5,873,868 A * | 2/1999 | Nakahata | 604/383 |
| 6,049,915 A * | 4/2000 | Malowaniec | 2/400 |
| 6,262,331 B1 * | 7/2001 | Nakahata et al. | 604/383 |

FOREIGN PATENT DOCUMENTS

| | | |
|---|---|---|
| DE | 195 09 953 A1 | 9/1996 |
| DE | 195 22 743 A | 12/1996 |
| EP | 0 750 893 A2 | 1/1997 |

* cited by examiner

*Primary Examiner* — Melanie Hand
(74) *Attorney, Agent, or Firm* — John G. Powell; George H. Leal; Jay A. Krebs

(57) ABSTRACT

An absorbent article having extensibility at waist panel is disclosed. The absorbent article includes a liquid pervious topsheet, an absorbent core disposed underneath the topsheet, and a chassis layer. A first or second waist panel includes a portion of the chassis layer. The chassis layer includes a plurality of spaced discontinuities regularly disposed in at least a portion of the first or second waist panel. The discontinuities are open to provide the chassis layer with extensibility in the transverse direction when the first or second waist panel is subjected to tension. The absorbent article also includes an extensibility controlling means to control the extensibility of the chassis layer.

16 Claims, 8 Drawing Sheets

ABSORBENT ARTICLE HAVING EXTENSIBILITY AT WAIST PANEL

CROSS REFERENCE TO RELATED APPLICATIONS

This application is a continuation application of prior copending International Application PCT/US02/20427 filed Jun. 28, 2002, designating the U.S., which claims the benefit of U.S. Application No. 60/302,431, filed Jul. 2, 2001.

TECHNICAL FIELD

This application relates to absorbent articles including, but not limited to, diapers, training pants, adult incontinence devices, diaper holders, feminine hygiene garments, and the like. More particularly, the present invention relates to absorbent articles having an extensible chassis layer whose extensibility is controlled by an extensibility controlling means.

BACKGROUND

Absorbent articles such as diapers, training pants, adult incontinence devices, diaper holders, feminine hygiene garments, and the like are designed to absorb and retain liquid and other discharges from the human body and to prevent body and clothing soiling. Absorbent articles are also designed to provide fitment force to prevent absorbent articles from sagging or sliding down on the body of the wearer during wear. Such fitment force can be provided by utilizing stretchable material around the waist panel of absorbent article. Several attempts have been made to make portions of absorbent articles stretchable in response to relatively low wearing forces exerted upon the absorbent articles. Typically, prior art solutions rely on the addition of traditional elastics such as natural or synthetic rubber. For example, traditional elastics have been secured to a portion of the waist panel of the absorbent article, such as a portion of the topsheet or a portion of the backsheet forming the waist panel. However, the portions of the topsheet and the backsheet are not normally elastic or stretchable. One approach to provide extensibility to the inelastic material is to subject the elastics and material to mechanical processing, e.g., ring-rolling, to permanently elongate the material to extend beyond its initial untensioned length and allow elastics to be effective. However, mechanical processing sometimes causes unexpected holes which are randomly created in the material which gives poor impression to the consumers. Otherwise, highly processable materials, e.g., having high modulus against strain, which is expensive, must be used to avoid such unexpected randomly created holes.

Thus, there is a need to provide an absorbent article having extensibility at the waist panel which can be formed cheaply and which provides aesthetics to the consumers.

SUMMARY

The present invention is relevant to an absorbent article having extensibility in at least one waist panel. The absorbent article of the present invention has a pair of longitudinal side edges and a first end edge and a second end edge, wherein a first waist panel is adjacent to the first end edge and a second waist panel is adjacent to the second end edge, a crotch panel positioned between the waist panels, and a side panel extending laterally outwardly from the first or second waist panel. The absorbent article comprises a liquid pervious topsheet, an absorbent core disposed underneath the topsheet, and a chassis layer. The first or second waist panel comprises a portion of the chassis layer. The chassis layer includes a plurality of spaced discontinuities regularly disposed in at least a portion of the first or second waist panel. The discontinuities are open to provide the chassis layer with extensibility in the transverse direction when the waist panel is subjected to tension. The absorbent article comprises an extensibility controlling means to control the extensibility of the chassis layer. The extensibility controlling means inhibits the chassis layer from extending beyond extensibility causing breakage of the chassis layer.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION

All cited references are incorporated herein by reference in their entireties. Citation of any reference is not an admission regarding any determination as to its availability as prior art to the claimed invention.

"Comprising" means that other steps and other elements which do not affect the end result can be added. This term encompasses the terms "consisting of" and "consisting essentially of."

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, wipes, mops, bandages and the like. The term "longitudinal," as used herein, refers to a line, axis or direction in the plane of the absorbent article that is generally aligned with (e.g., approximately parallel to) a vertical plane which bisects a standing wearer into left and right body halves when the absorbent article is worn. The terms "transverse" or "lateral" used herein, are interchangeable, and refer to a line, axis or direction which lies within the plane of the absorbent article that is generally perpendicular to the longitudinal direction.

Figure 1:
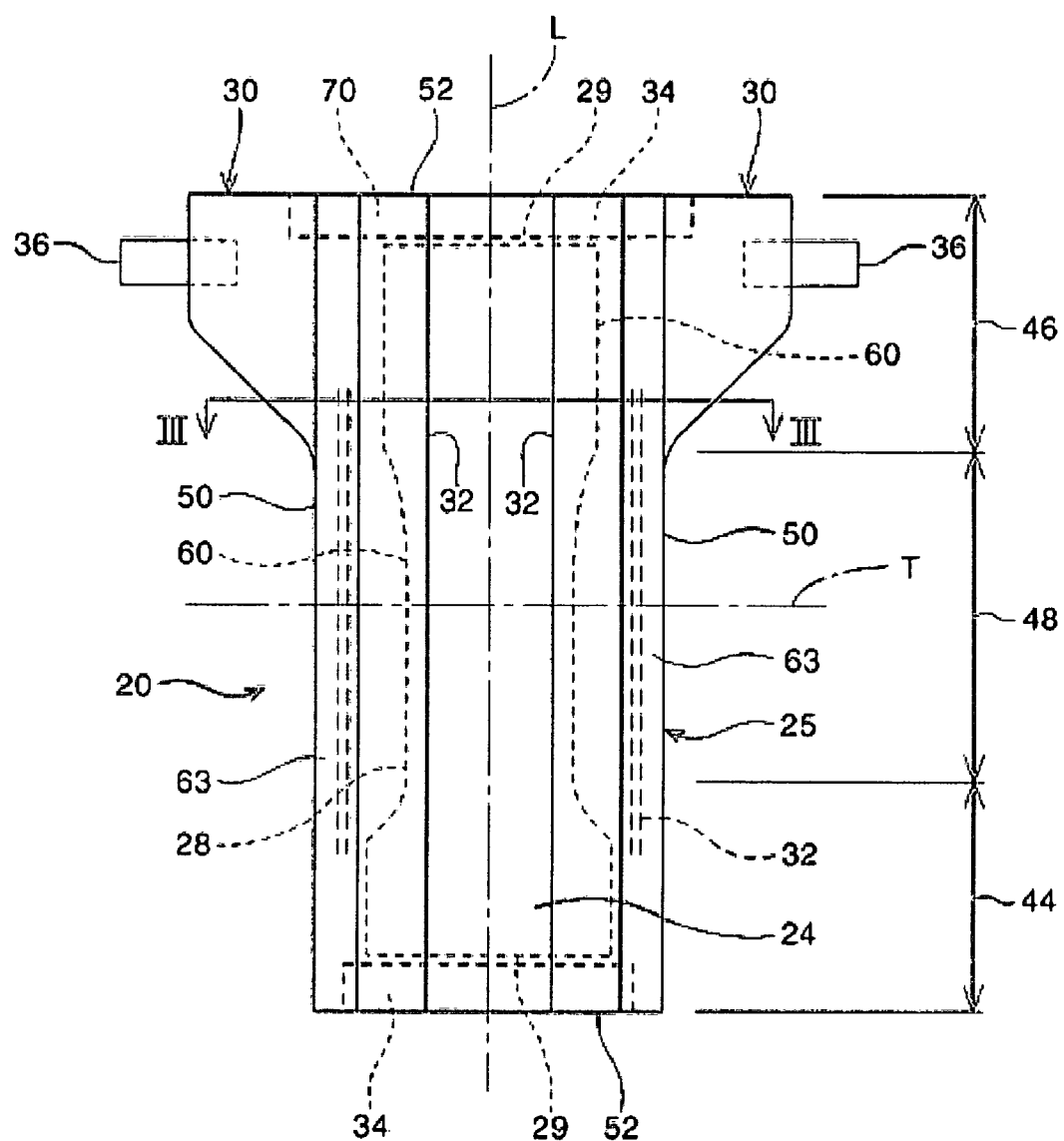
FIG. 1 is a plan view of a wearer facing surface of an absorbent article in accordance with the present invention, in the form of a disposable diaper.
Figure 2:
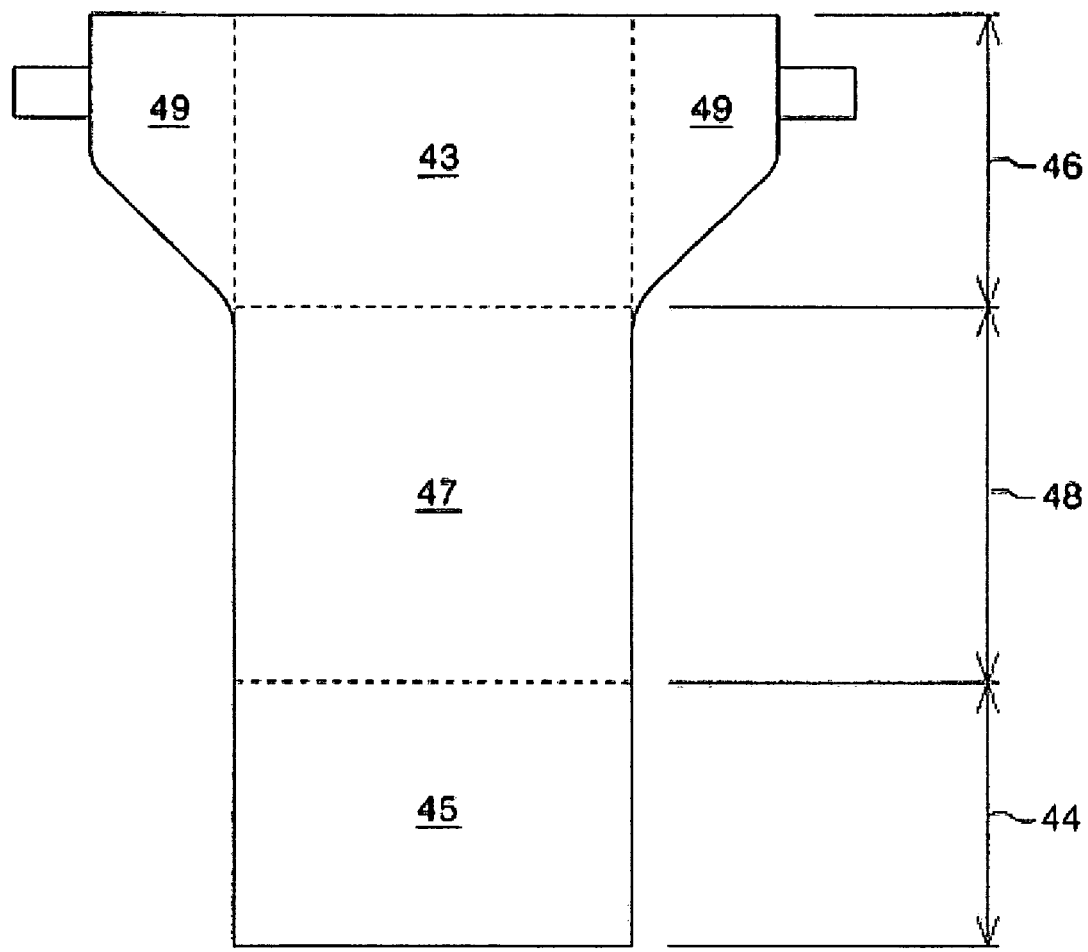
FIG. 2 is a simplified plan view of the absorbent article of the present invention showing the various panels of the article.

FIG. 1 is a plan view of the diaper 20 of the present invention in a flat-out, state. The portion of the diaper 20 that faces the wearer is oriented towards the viewer. The diaper 20 has two centerlines, a principal longitudinal centerline L and a principal transverse centerline T. The diaper 20 is shown in FIG. 1 to have a first waist region 46 (back waist region), a second waist region 44 (front waist region) opposed to the first waist region 46 and a crotch region 48 located between the first waist region and the second waist region. The periphery of the diaper 20 is defined by the outer edges of the diaper 20 in which the longitudinal side edges 50 run generally parallel to the longitudinal centerline L of the diaper 20 and the end edges 52 run between the longitudinal side edges 50 generally parallel to the transverse centerline T of the diaper 20. The diaper 20 has a first waist panel (back waist panel) 43 and a second waist panel (front waist panel) 45 disposed in the first waist region 46 and the second waist region 45, respectively, a crotch panel 47 positioned between the waist panels 43 and 45 and disposed in the crotch region 48, and a pair of side panels 49 extending laterally outwardly from the first waist panel 43 and disposed in the first waist region 46. In the embodiment shown in FIGS. 1 and 2, the side panel 49 extends from the first waist panel 43. Alternatively, the diaper 20 may also have side panels extending laterally outwardly from the second waist panel 45.

As shown in FIG. 1, the diaper 20 preferably comprises a main body 25 extending through the waist panels 43, 45 and the crotch panel 47; and ear portions 30 extending in the side panels 49. The main body 25 comprises a liquid pervious topsheet 24; an absorbent core 28 disposed underneath the liquid pervious topsheet 24; and an chassis layer 21 (refer to FIG. 3). The chassis layer 21 in the embodiment shown in FIG. 3 comprises a laminate formed by an outer sheet 23 and an inner sheet 26. The main body 25 may further comprise elasticized leg cuffs 32 and an elastic waist feature 34. The ear portion 30 is joined to the main body 25. The ear portion may have a fastening system generally designated by 36. In the embodiment shown in FIG. 1, the main body 25 and the ear portion 30 are formed with separate materials. Alternatively, the main body 25 and the ear portion 30 may be formed with a single integral material.

The topsheet 24 is preferably positioned adjacent the body-facing surface of the absorbent core 28 and may be joined thereto and/or to the chassis layer 21 by any attachment means known in the art. The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly.

The absorbent core 28 may comprise any absorbent material that is generally compressible, conformable, non-irritating to the wearer's skin, and capable of absorbing and retaining liquids such as urine and other certain body exudates. The absorbent core 28 has longitudinal side edges and end edges and can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In any case all or a portion of the core may include slits which allow the core to form openings when stretched into which fecal matter can flow. The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

The chassis layer 21 preferably comprises a continuous sheet or web which defines the first waist panel 43, the second waist panel 45 and the crotch panel 47. Thus, the chassis layer 21 is the primary stratum or layer of the diaper 20 (as used herein the term "layer" does not necessarily limit the element to a single strata of material in that a layer may actually comprises laminates or combinations of sheets or webs of the requisite type of materials). The chassis layer 21 may comprise a single layer of material. Alternatively, the chassis layer 21 may comprise two or more layers or may comprise two or more pieces connected into one piece of material.

The chassis layer 21 forms the exterior of the diaper 20, i.e., face away from the wearer. The chassis layer 21 is compliant, soft feeling, and non-irritating to the wearer's skin. A suitable chassis layer 21 may be manufactured from a wide range of materials, such as plastic films; woven or nonwoven webs of natural fibers (e.g. wood or cotton fibers), synthetic fibers (e.g. polyester or polypropylene fibers), or a combination of natural and synthetic fibers; or film-coated nonwoven webs. Preferably, the chassis layer 21 is hydrophobic. The chassis layer 21 is also preferably impervious to liquids (e.g., urine) so that it may also serve as the component which prevents exudates absorbed and contained in the absorbent core from wetting garments which contact the diaper such as bed sheets and undergarments (i.e., it acts as the traditional diaper backsheet). The chassis layer may also be breathable (pervious to air or water vapor) if desired. The chassis layer may also be elastic if desired.

Figure 3:
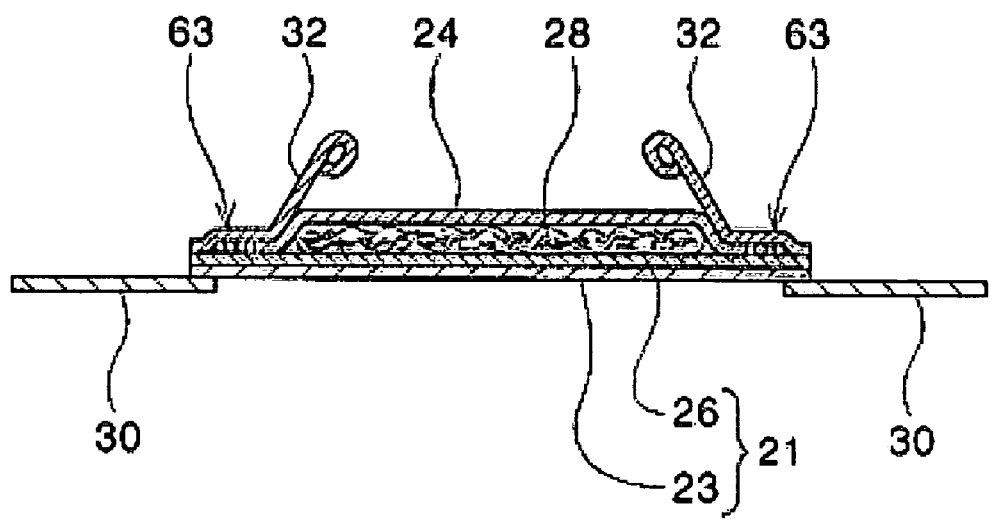
FIG. 3 is a cross sectional view taken along the line III-III of FIG. 1.

In the embodiment shown in FIG. 3, the chassis layer 21 comprises a laminate which is formed by the outer sheet 23 and the inner sheet 26 and which may be joined by any known means. The outer sheet 23 is preferably formed from a wide range of materials which may provide overall cloth-like appearance and feel such as woven or non-woven webs of natural fibers (e.g. wood or cotton fibers), synthetic fibers (e.g. polyester or polypropylene fibers), or a combination of natural and synthetic fibers. The outer sheet 23 may be made of a nonwoven containing thermoplastic fibers, typically 50% or more, preferably 100%. Preferably the outer sheet 23 is a carded nonwoven web of polypropylene fibers. A suitable outer sheet is Series 6700 Nonwovens manufactured by Scott Nonwovens of Landisville, N.J. The inner sheet 26 is preferably formed from a wide range of materials which provides liquid impermeability. Therefore, the inner sheet 26 is preferably a polymeric film. The inner layer 26 may comprise breathable materials. An example of such a film is that manufactured by Exxon Chemical Company under the tradename EXXAIRE. The outer sheet 23 and the inner sheet 26 are coextensive in the embodiment shown in FIGS. 1 and 3. Alternatively, the inner sheet 26 may be shorter in the longitudinal direction of the diaper than the outer sheet 23 to cover the area of the absorbent core 28. In this arrangement, the outer sheet 23 substantially serves as the chassis layer 21. The first waist panel 43 of the chassis layer 21 comprises only the outer sheet 23 while the rest of the panels (i.e., second waist panel 45 and crotch panel 47) comprise the outer sheet 23 and the inner sheet 26. Alternatively, the outer sheet 23 may be shorter in the longitudinal direction of the diaper than the inner sheet 26. In this arrangement, the inner sheet 26 substantially serves as the chassis layer 21.

The chassis layer 21 may comprise two or more pieces connected into one piece of material. For instance, the chassis layer may comprises one piece of a nonwoven extending only in the first waist panel 43 and one piece of plastic film which is liquid impervious and extends in the second waist panel 45 and the crotch panel 47. Each piece may be joined by any known means to form a chassis layer.

The chassis layer 21 may comprise a single layer of material such as a plastic film, a woven or a nonwoven web. When the chassis layer 21 comprises a single layer of a woven or a nonwoven, the diaper 20 may have a liquid impervious sheet disposed between the absorbent core 28 and the chassis layer 21 to prevent leakage of the liquid contained in the absorbent core 28. The liquid impervious sheet disposed between the absorbent core and the chassis layer may extend in the first waist panel 43, the second waist panel 45 and the crotch panel 47 to have the same length and the width as the chassis layer 21. Alternatively, the liquid impervious sheet may have shorter length and width than the chassis layer 21. The liquid impervious sheet may be joined by any known means to the chassis layer 21 in a portion of or in the entirety of the coextensive area of the liquid impervious sheet and the chassis layer 21. When the liquid impervious sheet has the same length and width as the chassis layer 21, it serves the substantially same function as the liquid impervious inner sheet 26 of the chassis layer 21 in the embodiment shown in FIGS. 1 and 3.

The first waist panel 43 positioned in the first waist region 46 comprises a portion of the chassis layer 21. The first waist panel 43 may further comprise a portion of the topsheet 24 and a portion of the absorbent core 28. Further the first waist panel 43 may comprise additional elements such as a waist band feature 34 and a leg elastic feature 32.

Figure 6:
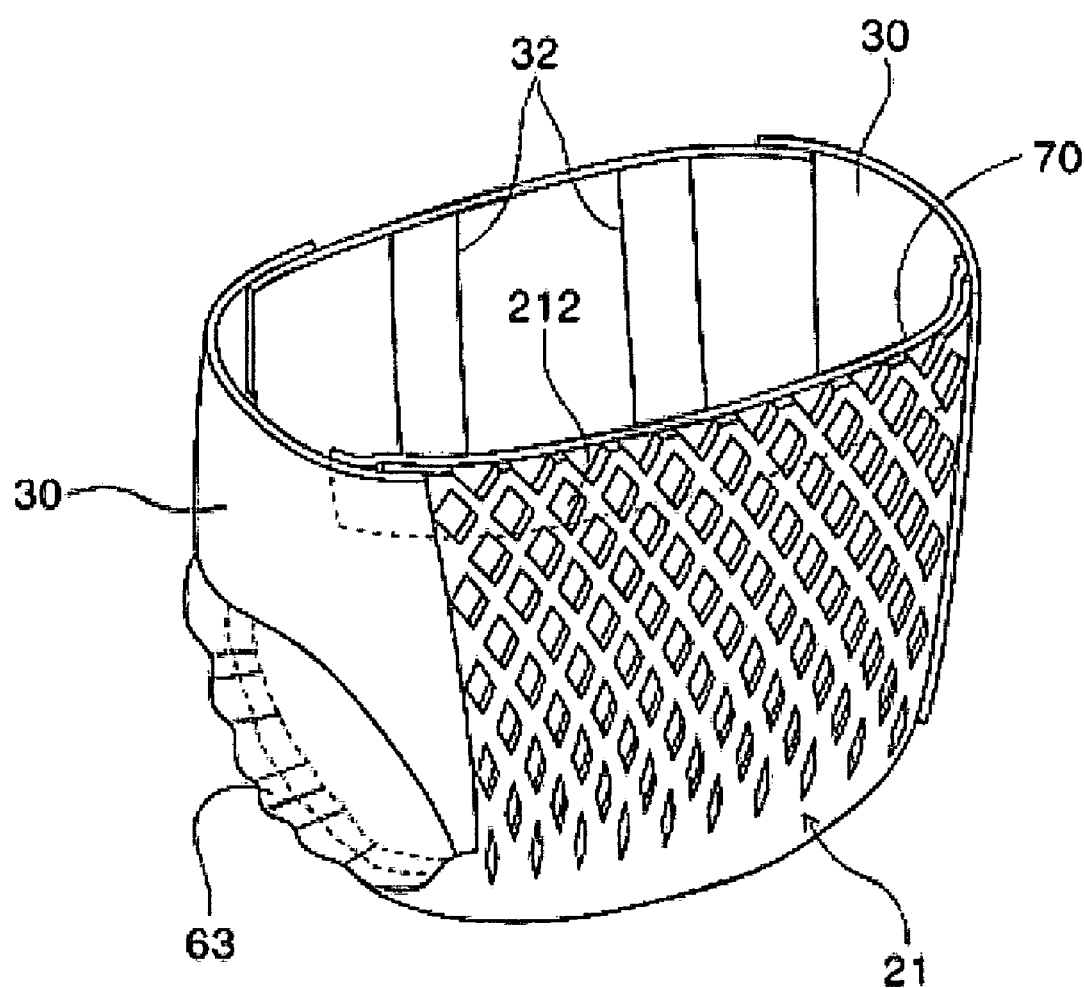
FIG. 6 is a perspective view of the absorbent article shown in FIG. 1, showing a configuration in use.

The chassis layer 21 of the first waist panel 43 in accordance with the present invention preferably includes one or more regions that when placed under tension includes a plurality of relatively small openings that extend through the chassis layer 21. Regions of the chassis layer 21 that are intended to present openings through the chassis layer when the chassis layer 21 is placed under laterally-directed tensile forces are preferably pierced by providing a plurality of discontinuities in the form of slits, cuts, or perforations that extend through the chassis layer 21. The discontinuities are arranged to define in the chassis layer 21 a predetermined pattern of discrete, localized regions of slits, cuts, or perforations. The discontinuities permit the edges of the chassis layer 21 that surround the discontinuities to separate from each other and thereby provide the desired plurality of small openings. Such discontinuities are preferably in the form of rectilinear cuts, curvilinear cuts, or combinations thereof, that can be made by a variety of cutting devices of the types known to those skilled in the art. Such a plurality of discontinuities allow the chassis layer 21 of the first waist panel 43 to have extensibility when placed under tension. Further, it also not only allows to provide aesthetics with the diaper when the diaper is worn as shown in FIG. 6, but is effective to communicate breathability to the consumers. Moreover, because the discontinuities are formed on the first waist panel 43 of the diaper, more specifically in the back waist region, the wearer does not tear the discontinuities or the possibility of the wearer's tearing the discontinuities at least reduces. Further, the caregiver typically inserts the waist panel of the diaper underneath the wearer's hip when the wearer lies and pulls the ear portions to fasten the diaper. In such a case, because the waist panel having discontinuities are hidden underneath the wearer, the caregiver does not tear the discontinuities or possibility of caregiver's tearing the discontinuities at least reduces.

Figure 4:
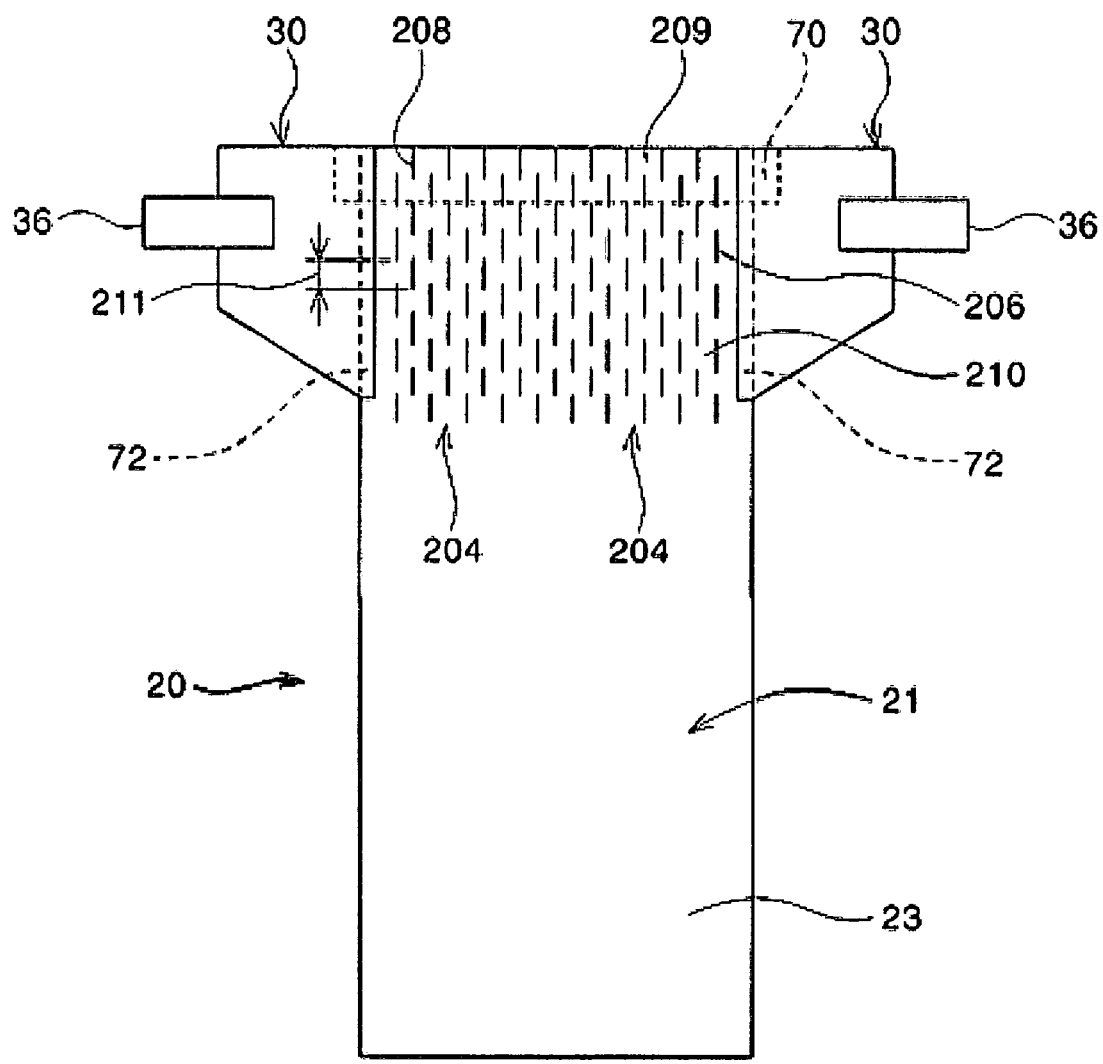
FIG. 4 is a plan view of a garment facing surface of the absorbent article shown in FIG. 1.

Referring now to FIG. 4, there is shown the garment-facing surface of a diaper 20 having a chassis layer 21 in accordance with the present invention. In all other respects the structure of diaper 20 is the same as that shown in FIG. 1 and described above in connection with diaper 20. As shown in FIG. 4, the chassis layer 21 of the first waist panel 43 includes a pattern 204 of discrete, spaced discontinuities defined by a plurality of rectilinear cuts or slits 206 that are regularly disposed in the chassis layer 21 and that extend through the chassis layer 21. While FIG. 4 depicts the configuration of the diaper in which the slits are provided on substantially the entire area of the first waist panel 43, the slits may be provided only a portion of the area of the first waist panel 43. Alternatively, the slit pattern 204 may be provided in a portion of the crotch panel 47. As used herein the term "regularly" refers to the configuration in which each discontinuity is spaced at regular intervals including, e.g., constant intervals or constantly varying intervals. Slits 206 are preferably oriented so that they extend in the longitudinal direction of diaper 20, in the direction of longitudinal centerline L (refer to FIG. 1), and they also are preferably aligned to define a plurality of laterally spaced columns 208 that also extend in the longitudinal direction of diaper 200. As they are shown in FIG. 4, the slits 206 are of substantially equal length, but they can be of different lengths, if desired. Also as shown in FIG. 4, the slits 206 of a given column 208 are longitudinally and equally spaced from each other, and adjacent columns 208 are at a transverse spacing 209 from each other and are positioned so that the ends of slits 206 of one column 208 are longitudinally offset from the ends of slits 206 of adjacent columns 208. Accordingly, laterally opposite the intervening uncut spaces between aligned slits 206 of one column 208 and slits 206 of the adjacent columns 208. As it is illustrated in FIG. 4, the chassis layer 21 is in its relaxed, untensioned condition, at a time when the slits 206 are in substantially closed condition in that the edges of the slits are substantially in contact with each other so as to make the chassis layer 21 appear to the naked eye to be a continuous chassis layer without cuts or slits. The discontinuities such as slits may be treated to strengthen the edge of the discontinuities when subjected to tension. For example, the treatment may be made by applying adhesive to the edge of the discontinuities to enhance the strength of the edge. Alternatively, the treatment may be made by joining materials to the edge of the discontinuities. Further, the treatment may be made by melting the edge of the discontinuities by, e.g., a heated cutter to form discontinuities (e.g., slits) when the chassis layer is made of thermoplastic material.

Figure 5:
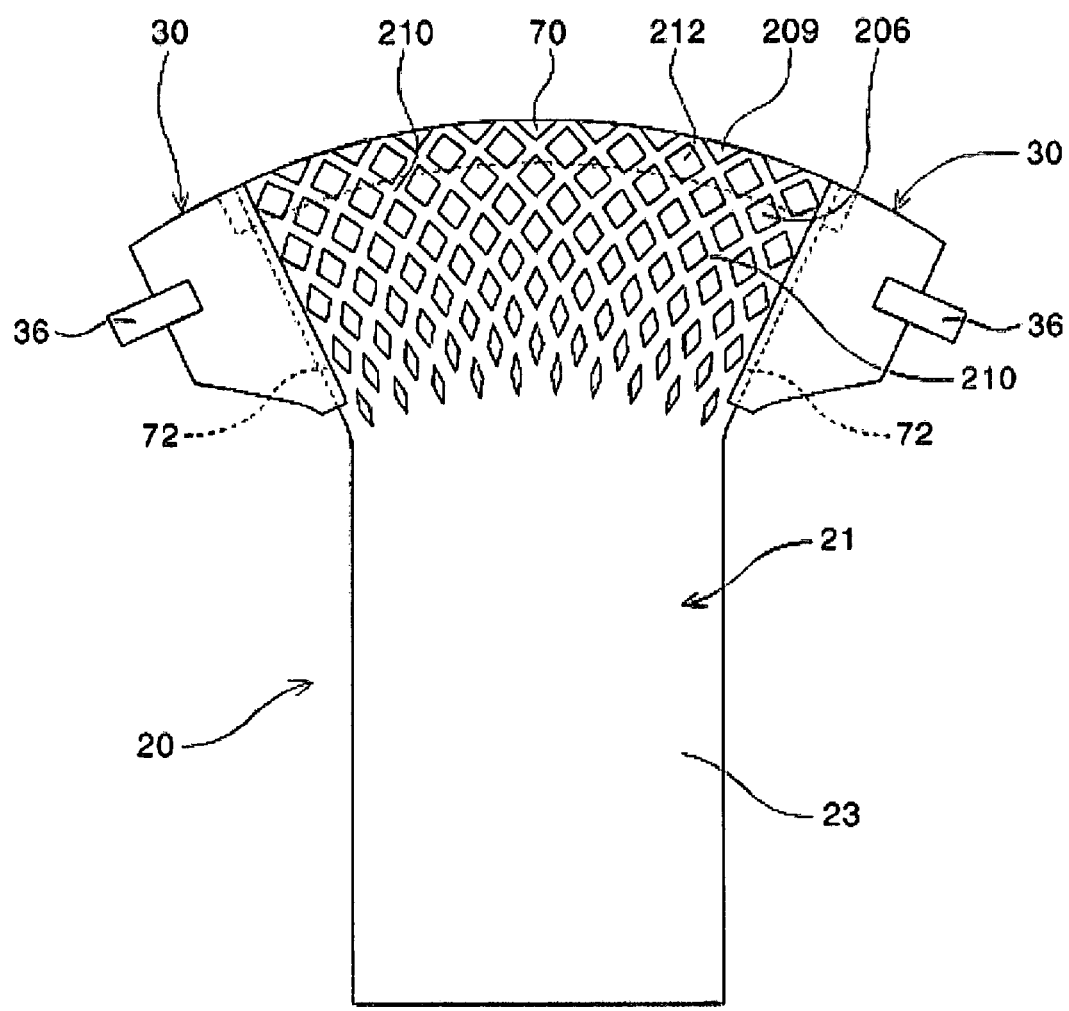
FIG. 5 is a plan view of a garment facing surface of the absorbent article shown in FIG. 1, showing a portion of the absorbent article subjected to tension in the transverse direction.

When laterally-directed tensile forces are applied to the chassis layer 21, the extensibility of the chassis layer 21 results in lateral stretching of the chassis layer 21. Under that condition, the uncut areas 210 between adjacent slits 206 are subjected to the laterally-directed tensile forces and they stretch in a lateral direction, causing edges of the slits 206 to separate from each other to provide individual openings 212, as shown in FIGS. 5 and 6. Because of the disposition, size, and spacing of slits 206 relative to each other, openings 212 are diamond-shaped, as shown in FIGS. 5 and 6. Such laterally-applied tensile forces are imposed when the ear portions 30 in the first waist region 46 of diaper 20 are each drawn laterally outwardly in opposite directions, to enable the diaper rear waist region to be drawn against the back of the wearer and around the wearer's waist so that ear portions 30 of the first waist area 46 at least partially overlap the second waist region 44.

The discontinuities (e.g., slits) are arranged to provide sufficient extensibility to the chassis layer of the waist panel. The chassis layer of the waist panel is able to extend without breakage up to 20%. Preferably, the chassis layer of the waist panel is able to extend without breakage up to 50%. More preferably, the chassis layer of the waist panel is able to extend without breakage up to 80%. Herein the percentage of the extension is the ratio of the extended length to the original length before extended. Therefore, when the chassis layer is extended up to 20%, the extend length of the chassis layer is 1.2 times as long as the original length. While the upper limit of the extensibility may be determined arbitrarily and is preferably as high as possible to avoid unexpected breakage of the chassis layer during the use of the diaper, it may be not more than 500%, preferably not more than 400%, more preferably not more than 350%.

When slits 206 in the chassis layer 21 are of rectilinear form, as shown in FIG. 4, the slits 206 can have a length of from about 1 mm to about 50 mm, preferably from about 2 mm to about 20 mm, and most preferably from about 3 mm to about 7 mm. The longitudinal spacing 210 between adjacent slits 206 can be up to about 10 mm, preferably up to about 5 mm, and most preferably up to about 2 mm. While the minimum longitudinal spacing may be arbitrarily determined, the longitudinal spacing 210 between adjacent slits 206 may be at least about 0.1 mm, preferably at least about 0.3 mm, most preferably at least about 0.5 mm. The transverse spacing 209 between adjacent columns 208 of aligned slits 206 can be up to about 10 mm, preferably up to about 3 mm, and most preferably up to about 1 mm. While the minimum lateral spacing may be arbitrarily determined, the lateral spacing 209 between adjacent columns 208 of aligned slits 206 may be at least about 0.1 mm, preferably at least about 0.2 mm, most preferably at least about 0.3 mm. The longitudinal offset 211 of the ends of the slits 206 in adjacent columns 208 can be from about 0 mm to about 50 mm, preferably from about 1 mm to about 10 mm, and most preferably from about 2 mm to about 4 mm.

Although shown in FIG. 4 as a series of parallel columns 208 of aligned slits 206 with constant intervals, slit pattern 204 can, if desired, be such that the slits of a given column are not precisely aligned with each other but are laterally offset from each other, staggered throughout all or a portion of the topsheet. Preferably, however, slits 206 are so disposed that the application of tensile forces to the chassis layer 21 results in a plurality of substantially equal area openings having an area of from about 1 $mm^2$ to about 2500 $mm^2$, that are substantially uniformly distributed over the entirety of cut pattern 204. Although openings 212 preferably are of substantially equal area, the areas of the openings need not be equal.

Figure 7:
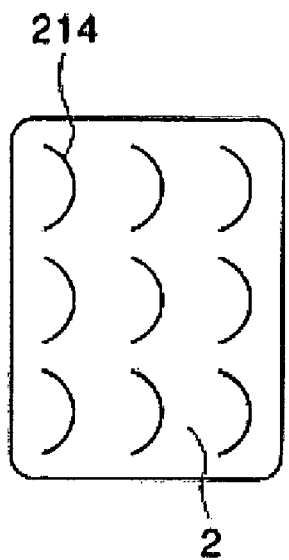
FIG. 7 is a fragmentary plan view of a portion of a chassis layer including curvilinear slits.
Figure 8:
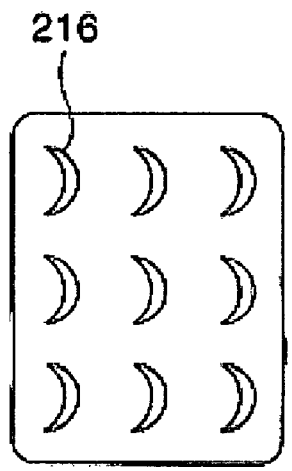
FIG. 8 is a view similar to that of FIG. 7 but showing the chassis layer of FIG. 7 when placed under tension.

Although slits 206 are shown in FIG. 4 as having a rectilinear form, they can alternatively be curvilinear or of any other suitable geometry. If desired, or a combination of rectilinear and curvilinear forms. One form of such curvilinear slits 214 is shown in FIG. 7. When the chassis layer 21 having the slit form and the column and row slit pattern shown in FIG. 7 is stretched laterally, the slits 214 open to define respective substantially crescent-shaped openings 216, as shown in FIG. 8.

Figure 9:
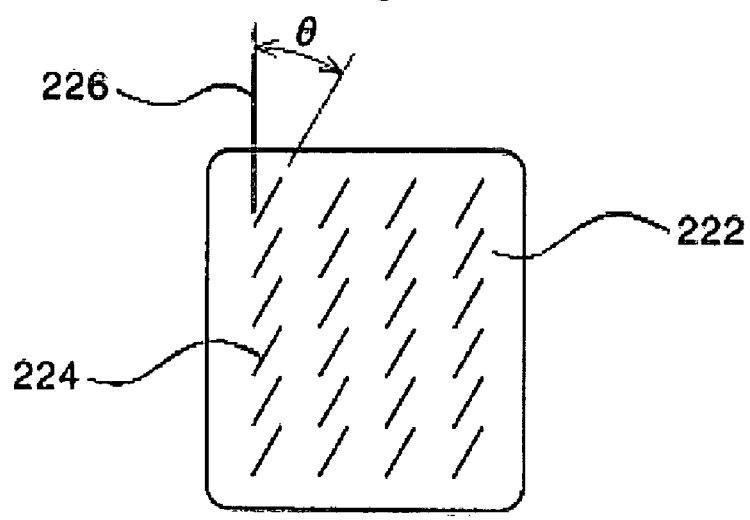
FIG. 9 is a fragmentary plan view of a portion of a chassis layer including a plurality of angularly disposed rectilinear slits.

In addition to the longitudinally aligned slits illustrated in slit pattern 204 shown in FIG. 4, the slit pattern can be arranged as shown in FIG. 9. As there shown, the individual slits in the chassis layer 21 can be disposed in a pattern 222 of angularly disposed slits 224. Although slits 224 are each defined by a straight line cut, and although slit pattern 222 of FIG. 9 defines a series of laterally spaced, longitudinal columns each defined by a plurality of slits 224, each of slits 224 is inclined at an acute angle θ relative to a line 226 that is parallel to the longitudinal axis of the diaper. The inclination angle θ preferably is less than about 45°, and more preferably is less than about 30°. Moreover, the slits 224 can each be disposed at the same inclination angle, as shown in FIG. 9, or, alternatively, the inclination angles of the slits can differ within slit pattern 222, to provide the chassis layer that have different areas in different regions of the chassis layer. Additionally, the slit pattern can include both rectilinear slits and curvilinear slits, if desired. The slit pattern 204 shown in FIG. 4 can, if desired, be an overall pattern that extends over the entire surface of the chassis layer 21.

Other members forming the first waist panel 43 preferably does not interfere with the extensibility of the chassis layer 21. Therefore, the other members also may be extensible with the chassis layer 21. Alternatively, the other members may be free from attachment to the chassis layer 21 of the waist panel 43 or any other member which interferes with the extensibility of the chassis layer 21.

Figure 10:
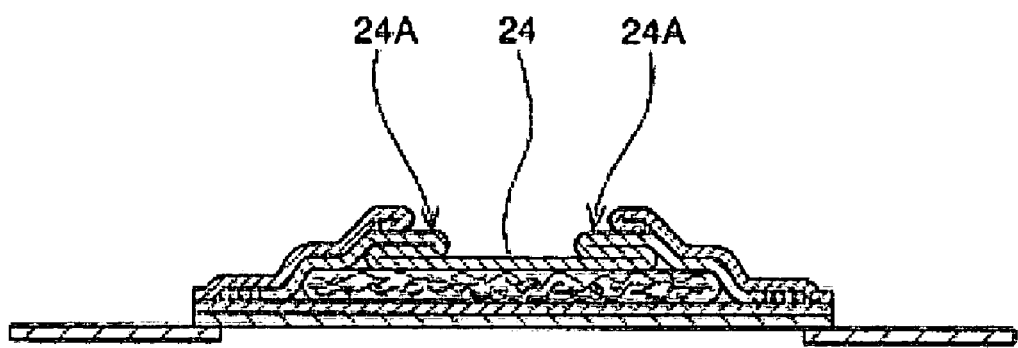
FIG. 10 is a cross-sectional view of another form of absorbent article.

The topsheet 24 forming the first waist panel 43 may be extensible, preferably has an extensibility beyond the extensibility causing breakage of the chassis layer 21 of the waist panel 43 so that the topsheet 43 and the chassis layer 21 each stretch laterally simultaneously when diaper 20 is applied to the body of a wearer. Such extensibility of the topsheet may be provided by using elastic materials for the topsheet. Instead of having the attribute of elastic extensibility, the topsheet 24 can alternatively be of a substantially inelastic nature, if desired. In that event, the topsheet 24 may have a width greater than the chassis layer, wherein, e.g., a portion of the topsheet may have pleats 24A such that the width of the pleated topsheet conforms to the width of the chassis layer as shown in FIG. 10. When the diaper is applied to the body of the wearer, the waist panel 43 is subjected to tension and the pleats 24A of the topsheet 24 extends so as not to interfere with the extension of the chassis layer 21 (i.e., causing slits 206 provided therein to open). Alternatively, the topsheet 24 may be provided with a plurality of discontinuities in the form of slits, cuts, or perforations that extend through the topsheet 24 and that may be the same pattern of discontinuities as provided in the chassis layer 21 or different pattern of discontinuities from that provided in the chassis layer 21.

The absorbent core 28 extending into and forming the first waist panel 43 is preferably not joined to the chassis layer 21 so as not to interfere with extensibility of the chassis layer. It is also preferable that the absorbent core 28 is not joined to the topsheet 24 if the topsheet 24 is formed by elastic material or is not joined to a portion of the topsheet 24 which is designed to extend when the waist panel 43 is subjected to tension. However, the absorbent core 28 may be joined to the chassis layer 21 so as to prevent the absorbent core 28 in the waist panel 43 from sagging during the use of the diaper. In that event, the absorbent core 28 is preferably joined to a portion of the chassis layer 21 along the longitudinal center line L of the diaper 20. This allows the rest of the portion of the chassis layer 21 to extend without being interfered by the absorbent core 28. Alternatively, the absorbent core 28 may be joined to a portion of the topsheet 24. Alternatively, the absorbent core 28 may not be extended into the waist panel in which the discontinuities are provided. This allows not only interference of the extensibility of the chassis layer but prevention of liquid leakage from the absorbent core through the discontinuities in the waist panel.

The diaper 20 also comprises an extensibility controlling means 70 to control the extensibility of the chassis layer 21. The chassis layer 21 may tear at discontinuities such as slits if the chassis layer 21 is extended beyond the extensibility causing breakage of the chassis layer 21. Therefore, the extensibility controlling means 70 is provided to inhibit the chassis layer 21 from extending beyond extensibility causing breakage of the chassis layer 21. Preferably, the extensibility controlling means 70 inhibits the chassis layer 21 from extending beyond 20% at tension force of 125 grams/25 mm, preferably at tension force of 500 grams/25 mm, more preferably 1000 grams/25 mm. The tension force applied to the chassis layer 21 is a force applied by a caregiver to extend the waist panel of the diaper to apply the diaper to the wearer. The performance of the extensibility control means can be determined by using a tensile tester suitable available from Instron Corporation (100 Royall Street, Canton, Mass. 02021, U.S.A.) as Code No. Instron 5564. The measurement is performed by applying the tension force (test force), which is correlated from 125 grams/25 mm based on the length of the longitudinal side edges of the waist panel, to the waist panel and the extensibility control means between the longitudinal side edges of the waist panel. The waist panel portion and the extensibility control means are together extended by the speed of 8.5 mm/sec. up until the tension force becomes the predetermined test force. The extensibility when the tension force becomes the test force is recorded. The recorded extensibility of the waist panel portion and the extensibility control means should not exceed extensibility causing breakage of the chassis layer 21

The extensibility controlling means 70 may comprise any material such as an elastic material or an inelastic material. In the embodiment shown in FIGS. 1, 4, 5 and 6, the extensibility control means 70 comprises an elastic waist band feature 34 that also facilitates to elastically expand and contract to dynamically fit the wearer's waist. The elastic waist band 34 inhibits the chassis layer 21 from extending beyond extensibility causing breakage of the chassis layer 21 by its resistive force against tension force. The elastic waist band 34 is preferably disposed along the transverse end edge 52 of the diaper 20. The elastic band 70 is preferably disposed in the first waist panel 43 in the transverse direction across at least the transverse width of the plurality of spaced discontinuities. In the embodiment shown in FIGS. 1 and 4, the elastic waist band 34 is disposed across the entire width of the first waist panel 43 in which the plurality of spaced discontinuities are provided. The elastic waist band 34 extends into the opposite ear portions 30 and are anchored thereto. Alternatively, the extensibility control means 70 may comprise an extensible topsheet material. While the extensible topsheet stated above is provided to facilitate smooth extensibility of the chassis layer 21, the extensible topsheet may serve as the extensibility controlling means. The inelastic topsheet having pleats 24A shown in FIG. 10 may also serve as the extensibility controlling means. The overall width of the inelastic topsheet when the pleats 24A are extended is limited below the extensibility causing breakage of the chassis layer 21 to inhibit the chassis layer 21 from extending beyond the extensibility causing breakage of the chassis layer 21. Alternatively, the extensibility control means may be any other elastic or inelastic material such as an elastic thread, an inelastic thread which is folded before the chaises layer is extended, an elastic film, or an inelastic film which is folded before the chaises layer is extended.

The diaper 20 may also comprise ear portions 30. The ear portion 30 is disposed in the ear panel 49. The ear portions 30 may be elastic or inelastic. The inelastic or less elastic ear portion 30 is effective in delivering the extension force applied by the fastening system 36 described hereinbelow to the extensible chassis layer 21 of the first waist panel 43. The elastic or extensible ear portion 30 provides a more comfortable and body-conforming fit by initially conformably fitting the diaper 20 to the wearer and sustaining this fit throughout the time of wear.

The inelastic or less elastic ear portion 30 may comprise any material such as plastic films; woven or nonwoven webs. The elastic ear portion 30 may comprises any material such as plastic films woven or nonwoven webs joined with elastic materials such as elastic films, elastic scrims, elastic strands, or any other elastic materials. The ear portion 30 may be a separate material from the chassis layer 21 and may be joined to thereto. Alternatively, the ear portion 30 may comprises an integral material forming the chaises layer 21. In the embodiment shown in FIGS. 1, 4 and 5, the ear portion 30 comprises an inelastic nonwoven material and joined to the chassis layer 21 at the seam 72.

The diaper 20 may also include a fastening system 36. The fastening system 36 preferably maintains the ear portion 30 of the first waist region 46 and the second waist region 44 in at least partially overlapped condition to provide lateral tensions about the circumference of the diaper 20 when it is worn, to hold the diaper 20 on the wearer. The fastening system 36 preferably comprises securement members that can be in the form of tape tabs that engage a landing member (not shown), and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 preferably further includes leg cuffs 32 that provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above. In addition to leg cuffs 32, diaper 20 can also include an elastic gasketing cuff 63 with one or more elastic strands positioned outboard of the barrier cuff.

Although particular embodiments of the present invention have been illustrated and described, it would be apparent to those skilled in the art that various other changes and modifications can be made without departing from the spirit of the present invention. It is therefore intended to cover in the appended claims all such changes and modifications that are within the scope of this invention.

What is claimed is:

1. An absorbent article having a pair of longitudinal side edges and a first end edge, a second end edge, a first waist panel adjacent to the first end edge, a second waist panel adjacent to the second end edge, a crotch panel positioned between the first and second waist panels, and a side panel extending laterally outwardly from the first or second waist panel, the absorbent article comprising a liquid pervious topsheet, an absorbent core disposed underneath the topsheet, and a chassis layer, wherein at least one of the first and second waist panels comprise a portion of the chassis layer, the chassis layer including an inner sheet and an outer sheet joined to one another to form a laminate, a plurality of spaced discontinuities regularly disposed in at least a portion of the first or second waist panel such that when the waist panel is subject to tension the discontinuities provide openings that extend through the laminate of the chassis layer thereby providing the chassis layer with extensibility in the transverse direction; and an elastic waist band configured as an extensibility controlling means, wherein the elastic waist band inhibits the chassis layer from extending beyond 20% at a tension force of 125 grams/25 mm.

2. The absorbent article of claim 1 wherein the extensibility causing breakage of the chassis layer is more than 20%.

3. The absorbent article of claim 2 wherein the extensibility controlling means is disposed in the first or second waist panel in the transverse direction across at least the transverse width of the plurality of spaced discontinuities.

4. The absorbent article of claim 3 wherein the extensibility controlling means is disposed along the end edge.

5. The absorbent article of claim 1 wherein the chassis layer comprises a liquid impervious material.

6. The absorbent article of claim 1 wherein the absorbent article comprises a liquid impervious sheet disposed between the absorbent core and the chassis layer.

7. The absorbent article of claim 5 wherein the absorbent core does not extend into the first or second waist panel in which the discontinuities are provided.

8. The absorbent article of claim 6 wherein the absorbent core does not extend into the first or second waist panel in which the discontinuities are provided.

9. The absorbent article of claim 1 wherein the discontinuities are selected from the group consisting of: slits, cuts, and perforations.

10. The absorbent article of claim 9 wherein the discontinuities comprise a plurality of cuts wherein the cuts comprise rectilinear cuts, curvilinear cuts, or combinations thereof.

11. The absorbent article of claim 1 wherein the discontinuities are regularly disposed in the chassis layer.

12. The absorbent article of claim 1 wherein the discontinuities are oriented such that the discontinuities extend in a longitudinal direction.

13. The absorbent article of claim 12 wherein the discontinuities are aligned such that the discontinuities form a plurality of laterally spaced columns which extend in the longitudinal direction.

14. The absorbent article of claim 1 wherein the discontinuities comprise a plurality of edges wherein the edges are treated to strengthen the edges.

15. The absorbent article of claim 1 wherein the discontinuities are arranged such that the application of a tensile force to the chassis layer results in a plurality of equal area openings having an area from about 1 $mm^2$ to about 2500 $mm^2$.

16. The absorbent article of claim 1 wherein the discontinuities are arranged such that the application of a tensile force to the chassis layer results in a plurality of openings having an area from about 1 $mm^2$ to about 2500 $mm^2$.

* * * * *